United States Patent
Zardi et al.

[11] Patent Number: 5,882,606
[45] Date of Patent: Mar. 16, 1999

[54] METHOD OF RETROFITTING A HETEROGENEOUS EXOTHERMIC SYNTHESIS REACTOR

[75] Inventors: Umberto Zardi, CH-6900 Breganzona, Switzerland; Giorgio Pagani, Milan, Italy; Ermanno Filippi, Vacallo, Switzerland

[73] Assignees: Ammonia Casale S.A., Lugano/Besso; Umberto Zardi, Breganzona, both of Italy

[21] Appl. No.: 739,814

[22] Filed: Oct. 30, 1996

Related U.S. Application Data

[63] Continuation of Ser. No. 331,087, Oct. 28, 1994, abandoned.

[30] Foreign Application Priority Data

Oct. 29, 1993 [CH] Switzerland ............... 03 257/93-3

[51] Int. Cl.⁶ .......................................... B32B 27/04
[52] U.S. Cl. ..................... 422/148; 422/190; 422/201; 423/360; 423/361; 423/659
[58] Field of Search ................... 422/148, 190, 422/191, 192, 193, 194, 201; 423/360, 361, 659

[56] References Cited

U.S. PATENT DOCUMENTS

| 4,554,135 | 11/1985 | Grotz et al. | 422/144 |
|---|---|---|---|
| 4,744,966 | 5/1988 | Grotz | 423/360 |
| 4,755,362 | 7/1988 | Zardi | 422/148 |
| 4,935,210 | 6/1990 | Zardi et al. | 422/148 |
| 5,152,997 | 10/1992 | Zardi et al. | 422/148 |
| 5,236,671 | 8/1993 | Grotz | 422/148 |

FOREIGN PATENT DOCUMENTS

| 0355303 | 2/1990 | European Pat. Off. . |
| 0390420 | 10/1990 | European Pat. Off. . |
| 8634276 | 11/1991 | Germany . |

OTHER PUBLICATIONS

EP 202454 (Derwent Abstact) Nov., 1986.

*Primary Examiner*—Timothy McMahon
*Attorney, Agent, or Firm*—Sughrue, Mion, Zinn, Macpeak & Seas, PLLC

[57] ABSTRACT

In a method of modernizing a heterogeneous exothermic synthesis reactor (1) of the type comprising an external shell (2), in which at least one catalytic bed (15, 16, 17) is supported, the catalytic bed (15, 16, 17) is connected to an external boiler (21), for generating high pressure steam, by means of a reacted gas outlet nozzle (4) and a conduit (29) extending in said nozzle (4) thereby forming an annular airspace (30). Advantageously, the airspace (30) defines an outlet flowpath of the gases cooled in the boiler (21) which avoids overheating of the nozzle (4).

6 Claims, 3 Drawing Sheets

METHOD OF RETROFITTING A HETEROGENEOUS EXOTHERMIC SYNTHESIS REACTOR

This is a Continuation of application Ser. No. 08/331,087 filed Oct. 28, 1994 now abandoned.

FIELD OF APPLICATION

From a general point of view, this invention refers to a method of modernizing reactors for effecting heterogeneous exothermic synthesis.

More particularly, the invention refers to a method of modernizing an ammonia or methanol synthesis reactor of the type comprising an external shell, in which at least one catalytic bed is supported which is in fluid communication with a nozzle extending below said shell, said nozzle being provided with an opening for withdrawing the reaction products leaving said at least one catalytic bed.

In the following description and in the claims, the term: modernizing, indicates the modification of a pre-existing reactor, with the aim of improving its performance and obtaining, for example, a production capacity and/or reaction efficiency comparable to those of a newly-built reactor.

In the terminology used in the field, this kind of modernization is also referred to with the terms: retrofitting or revamping.

In the modernization of reactors for heterogeneous synthesis, and in particular exothermic ones, the need of recovering to a higher thermal level the heat generated during the reaction while maintaining as unaltered as possible the external structure of the reactor, with particular regard to the shell, the cover and the gas outlet nozzle of the reacted gases, is more and more felt.

A prevailing importance is acknowledgedly given to the preservation of the external structure of the reactor, since any modification of the latter could render the desired modernization not only economically unfeasible, but also potentially dangerous owing to possible structural yieldings of the reactor in the modified areas.

BACKGROUND ART

The retrofitting methods according to the known art, fundamentally propose the mere substitution of the internals within the shell, in particular of the pre-existing catalytic bed or beds, with new radial or axial-radial high-yield beds.

Although these modernization methods allow to obtain, on the one hand, an increase of the reactor production capacity and/or conversion yield while maintaining the external structure thereof unaltered, they fail on the other hand to attain a recovery at an increased thermal level of the heat generated during the synthesis reaction.

In almost all cases, in fact, the reactor gas outlet nozzle is not able to withstand the temperature of the reaction gases leaving the lowermost catalytic bed, up to the point that they must be cooled before being discharged to the outside.

The need of maintaining the external structure of the synthesis reactor unaltered therefore allows the known modernization methods only a recovery of the heat possessed by the reaction products to a limited thermal level, which recovery does not exceed a pre-heating of boiler feed water or production of low pressure steam (less than 40 bar).

SUMMARY OF THE INVENTION

The problem underlying the present invention is, therefore, that of providing a method of modernizing a heterogeneous exothermic synthesis reactor, which allows to recover at a higher thermal level the reaction heat generated in the synthesis reactor, while maintaining the external structure of the reactor substantially unaltered.

The above problem is solved by a method as indicated hereinabove, wherein it comprises the steps of:

provided a boiler for generating high pressure steam outside said shell;

connecting the boiler to the shell in proximity of said nozzle;

connecting said at least one catalytic bed with an inlet collector in said boiler by means of a conduit extending in said nozzle thereby forming an annular airspace;

said conduit and airspace defining respective flowpaths for the reacted gases to said boiler and from said boiler to the outside of the reactor.

Advantageously, the modernization method of the invention allows a recovery of the reaction heat at a high thermal level, thus permitting the exploitation of hot gases having a temperature far higher than the design temperature of the reactor gases outlet nozzle. Such a recovery may be carried out in an extremely efficient manner, for example by producing high pressure steam (80–120 bar, 250°–350° C.), in a boiler placed outside of the reactor.

To this end, the method of the invention provides the step of connecting the catalytic bed, or the lowermost of the reactor catalytic beds, to the above mentioned boiler by means of a conduit, extending in the outlet nozzle of the reaction products, with which forms an annular airspace.

In this way, the reaction products, which leave the lowermost catalytic bed at high temperature, arrive directly to the boiler without coming into direct contact with the nozzle, from which they are divided by said airspace. This airspace, which is passed through by the gas cooled in the boiler where it has generated high pressure steam, assures that, in operation, the nozzle temperature does not exceed the design values.

In a particular and advantageous embodiment of the retrofitting method, said boiler is joined to the synthesis reactor by connecting to one another the shell and boiler gas outlet nozzles.

Preferably, the conduit for feeding the reaction products to the boiler is co-axially extended in the gas outlet nozzle, thus allowing a uniform cooling of its walls.

The method of the invention therefore allows an optimal recovery of the heat possessed by the reaction products without the need neither to substitute nor to modify the gas outlet nozzle.

Advantageously, the catalytic bed or the lowermost of the reactor catalytic beds, is connected to the boiler feed conduit through gas collecting and conveying means already existing in the reactor, further limiting in this way the modifications to be made to the reactor structure and thus decreasing the modernization cost.

The method according to the invention may also be advantageously carried out in combination with other known retrofitting methods which aim towards an efficiency increase of the reactor.

In accordance with another aspect of the invention, a method is provided for effecting heterogeneous exothermic synthesis with heat recovery at high thermal level, of the type comprising the steps of:

feeding gaseous reactants to at least one catalytic bed supported within a synthesis reactor;

reacting said gaseous reactants in said at least one catalytic bed;

removing from the reactor the reaction products leaving said at least one catalytic bed by means of a nozzle extending below said reactor and provided with a respective gas outlet opening, wherein it further comprises the steps of:

feeding the reaction products leaving said at least one catalytic bed to a boiler, outside the reactor, by means of a conduit extending in said nozzle thereby forming an annular airspace;

cooling the reaction products in said boiler with a simultaneous generation of high pressure steam;

removing the cooled reaction products leaving said boiler by means of said airspace and said gas outlet opening.

The method obtained in this way permits, in a reactor modernized according to the retrofitting method described above, to exploit the heat of the product leaving one of a plurality of catalytic beds, to produce, preferably, high pressure steam.

Preferably, the reaction products are fed to the boiler after traversing the lowermost catalytic bed before being finally removed from the reactor.

The characteristics and advantages of the invention will be better apparent from the description of an example of a modernization method according to the invention, given hereinbelow, by way of illustration but not of limitation, with reference to the attached drawings.

DETAILED DESCRIPTION OF A PREFERRED EMBODIMENT

Figure 1:
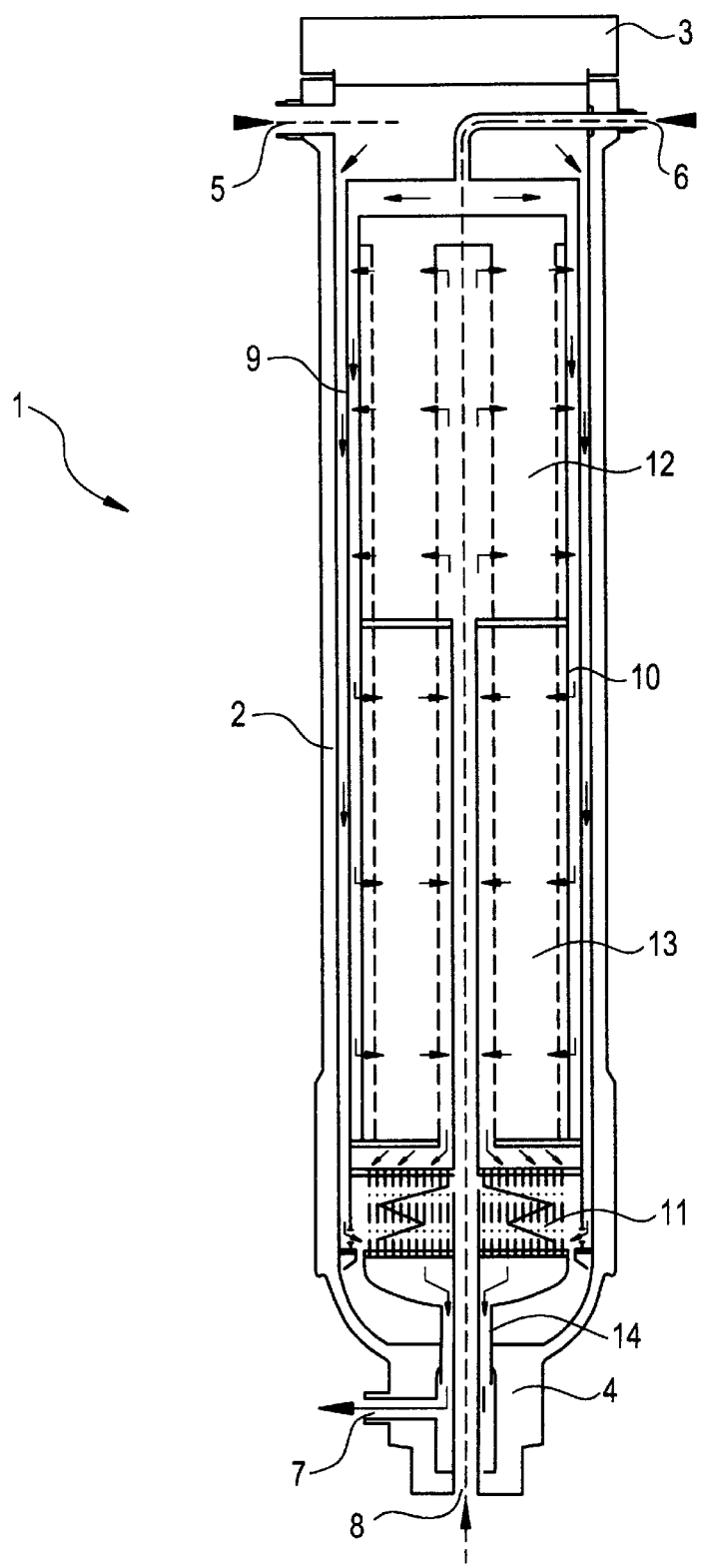
FIG. 1 shows a longitudinal section view of a reactor for heterogeneous exothermic synthesis according to the prior art.

With reference to FIG. 1, numeral 1 indicates a known heterogeneous exothermic synthesis reactor, i.e. for the production of ammonia or methanol.

Reactor 1 comprises a tubular lining or shell 2, closed on the upper side by a gas-seal cover 3 and provided on the lower side with an outlet nozzle 4 for the outlet of the reaction products.

The nozzle 4 is in turn provided with an outlet opening 7 for the reaction products, and with an opening 8 for feeding into the reactor a first part of the gaseous reactants.

A first opening 5 for feeding into the reactor a second part of gaseous reactants and a plurality of spaced-apart openings 6 (only one of which is shown in FIG. 1), for feeding into the reactor a third part of gaseous reactants or "quench" gases, are provided through the shell 2 in the proximity of the cover 3.

A cartridge 9 comprising in its upper part a reaction section 10 and, in its lower part, a heat exchanger 11, is conventionally supported within the shell 2. In this case, the reaction section 10 is made up of two catalytic beds 12 and 13, wherein granular or pellet-type catalyst is loaded, which are in fluid communication with nozzle 4, through a conduit collector 14.

In FIG. 1, the gases flowpaths across the catalytic beds 12 and 13 and the heat exchanger 11—provided to cool the reaction products before the latter leave the reactor through nozzle 4—are shown.

It should be mentioned in this respect that, owing to this cooling, the nozzle 4 can withstand a maximum temperature much lower than the temperature of the products which leave the reaction section.

Figure 2:
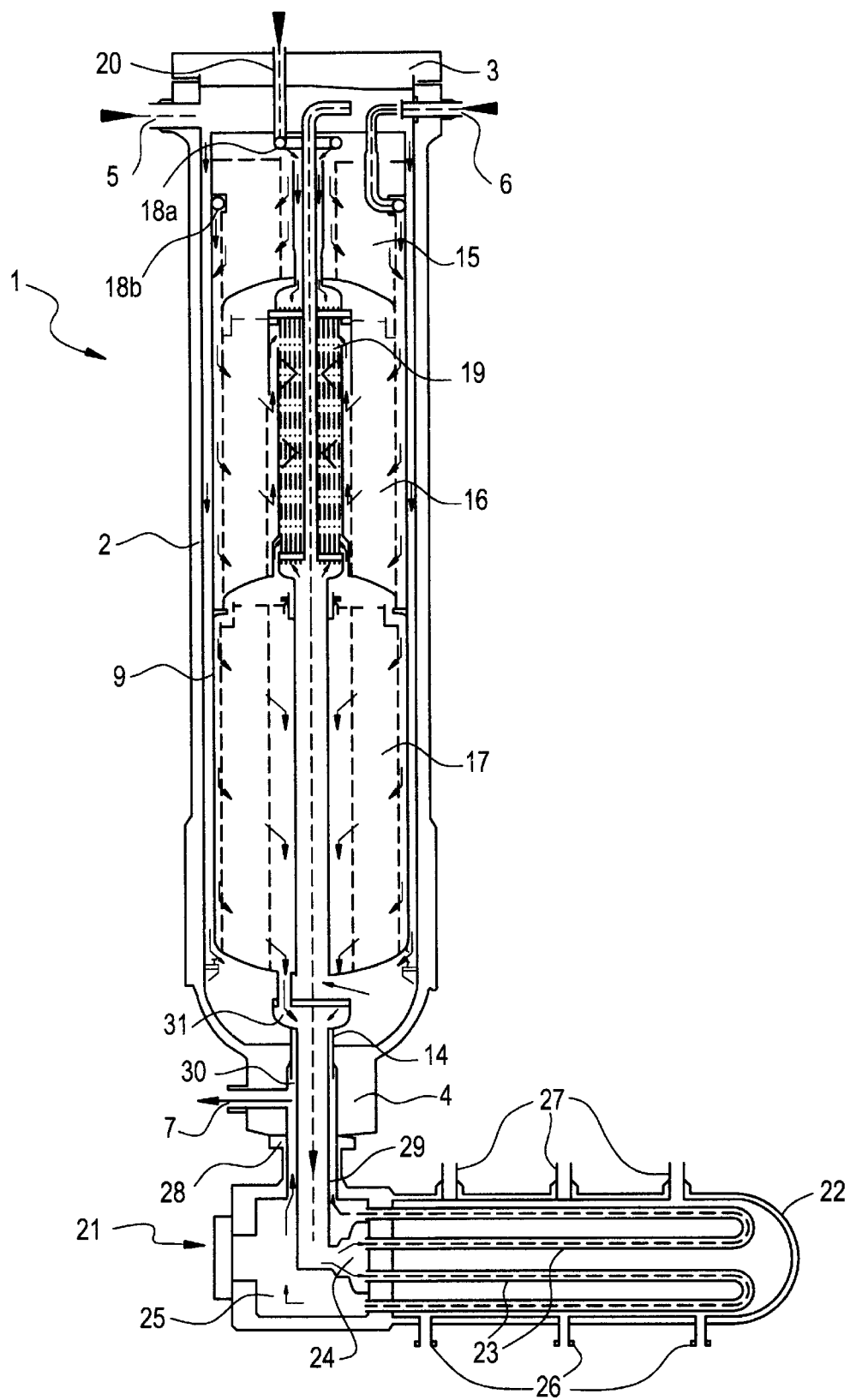
FIG. 2 shows a longitudinal section view of a reactor obtained by modifying the reactor shown in FIG. 1 with the modernization method according to the present invention.

In FIG. 2 a reactor for heterogeneous exothermic synthesis, obtained by modifying the reactor in FIG. 1 according to the modernization method of the invention, is shown.

In this Figure, the details of reactor 1 which are structurally and functionally equivalent to those illustrated in FIG. 1, shall be indicated with the same reference numbers and shall not be further described.

In FIG. 2 the arrows indicate the various gas flowpaths to and from the reactor 1.

In accordance to a particularly advantageous embodiment of the present invention, the cartridge 9 of the reactor shown in FIG. 1 is first emptied of its internals and equipped with catalytic beds 15, 16 and 17 of the axial-radial flow type, with intermediate quench type cooling (by mixing with cold synthesis gas) and indirect type cooling. (by means of a heat exchanger), according to retrofitting methods known in the art.

To this end, quench gas distributors 18a, 18b are provided upstream of the first and second catalytic beds 15, 16, while a gas/gas heat exchanger 19 is arranged upstream of the third catalytic bed 17.

The inlet of quench gas to the distributor 18a takes place by means of a conduit 20 passing through the cover 3.

After having modified the reactor 1 in such a way, the retrofitting method of the present invention includes, in a first step, providing outside the reactor a boiler 21, in this case of the type suitable to produce high pressure steam.

The boiler 21, which in the example illustrated in FIG. 2 is of the shell-and-tube type, comprises an external shell 22 which conventionally supports a plurality of tubes 23, the opposite free ends thereof being open on tube-side inlet and outlet collectors 24 and 25.

The boiler 21 also comprises a plurality of inlet nozzles 26 and outlet nozzles 27 for flowing shell-side a suitable cooling fluid, for example water.

With 28 is finally indicated a nozzle for withdrawing from the boiler 21 the tube-side flowing gas.

In a second step of the method, the boiler 21 is joined to the reactor 1 by connecting the nozzles 4 and 28 to one another, in a way known in the art, for instance by means of a plurality of conventional bolts, which are not shown.

During a further step, the lowermost catalytic bed 17 is connected tube-side to the inlet gas collector 24 of the boiler 21 through a conduit 29 extending in the nozzle 4, with which it forms an annular airspace 30.

A gas collecting chamber 31, integral with the conduit 28 is fixed gas tight to the conduit 14, avoiding any possible fluid leakage from the airspace 30 to the inside of reactor 1.

Therefore, at the end of said operations, the conduit 29 and the airspace 30 define respective gas flowpaths which allow the hot reaction products leaving the lowermost catalytic bed 17 to be sent to the boiler 21 and then to be discharged outside the reactor, after being cooled in the boiler.

Figure 3:
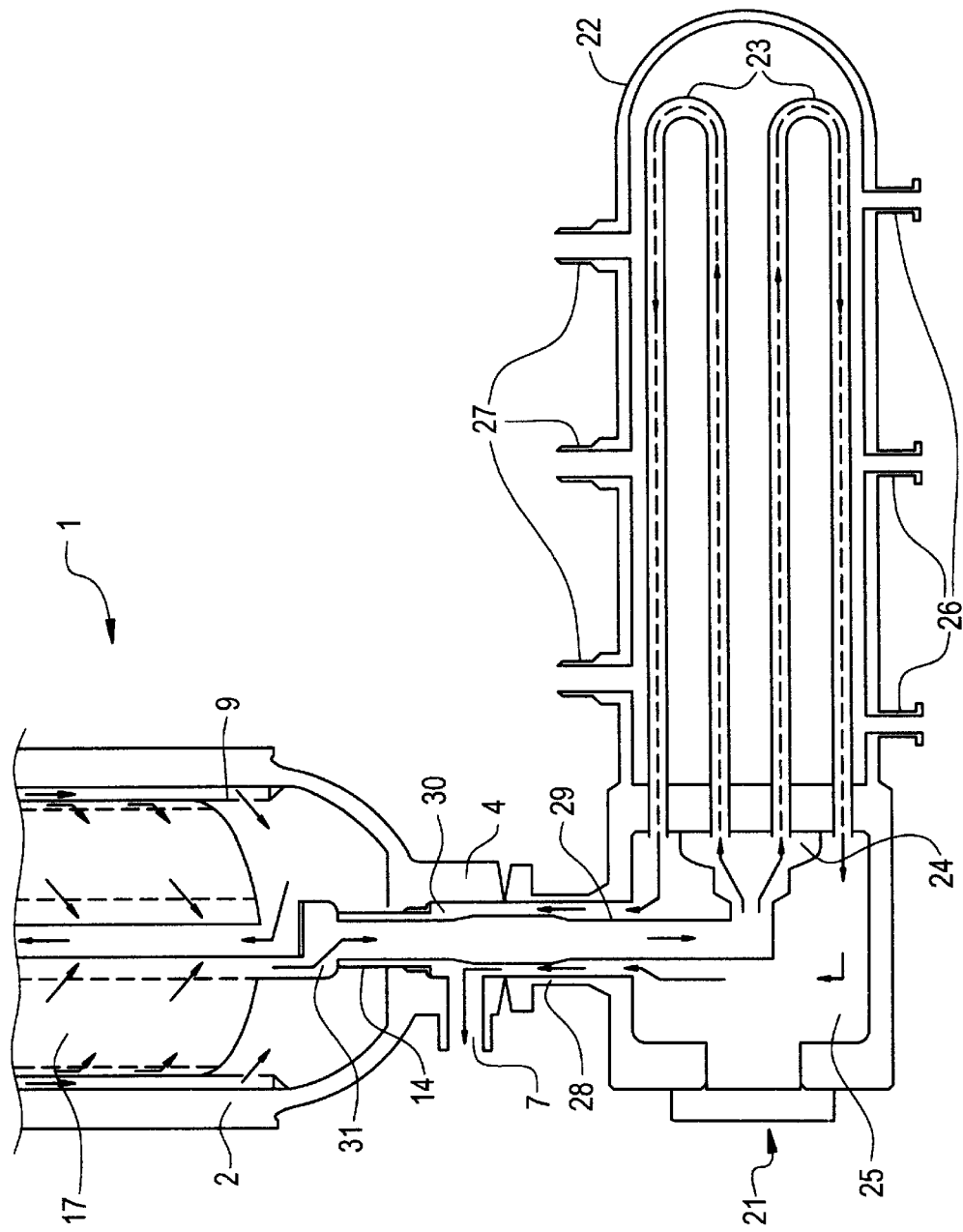
FIG. 3 shows a longitudinal section view, on an enlarged scale, of some particulars of the reactor shown in FIG. 2.

As shown in FIGS. 2 and 3, the gas flows from the boiler 21 directly to the outside of the reactor 1 without being circulated through any catalytic bed.

By means of the so retrofitted reactor 1, it is then possible to carry out heterogeneous exothermic synthesis with heat recovery at high thermal level in the following way.

The gaseous reactants fed to the reactor 1 through the opening 5 are pre-heated in the exchanger 19 and fed to the first catalytic bed 15, which is passed through with an axial-radial flow of centrifugal type, after being mixed with a first part of quench gas fed by distributor 18a.

The mixture reaction products/reactants leaving the first catalytic bed 15 is then sent to the second catalytic bed 16 after being mixed with a second part of quench gas fed by distributor 18b.

This mixture, which passes through the second bed 16 with an axial-radial centripetal flow, is then partially cooled by exchanger 19, before being fed to the third and last catalytic bed 17 still with an axial-radial centripetal flow.

By means of the conduit 29, the reaction products leaving the last catalytic bed 17 are fed, at a temperature of about 450° C., to the boiler 21, in which they are cooled to a temperature of about 330°–350° C., with a simultaneous generation of high pressure steam. The reacted gas leaving the boiler 21 is then removed from the reactor 1 through the airspace 30 and the opening 7 provided in the nozzle 4.

Since the reaction products flowing in the airspace 30 remove heat from nozzle 4, the method of the present invention permits to keep the nozzle at the design temperature, allowing economic and operating advantages due to a substantial preservation of the external structure of the reactor to be retrofitted.

Obviously, the heat of the reacted gases can be further used to heat another fluid, or to pre-heat the fresh synthesis gas in others heat exchange devices provided downstream of the boiler 21.

To the aim of accomplishing specific and occasional application requirements, the retrofitting of a synthesis reactor according to the present invention may be carried out providing further modifications, all included within the scope of protection defined by the following claims.

Thus, for example, the heat exchanger 11 of reactor 1 may be advantageously installed downstream of the reactor so as to pre-heat fresh synthesis gas with the residual heat of the reacted gas leaving boiler 21.

As an alternative, it is also possible to avoid the replacement of the catalytic beds 12 and 13 and of the heat exchanger 11 of reactor 1, by providing suitable means which allow the fluid communication between the lowermost catalytic bed and the conduit 29, by-passing heat exchanger 11.

We claim:

1. A method of making a modernized heterogeneous exothermic synthesis reactor comprising the following steps:

providing a heterogeneous exothermic synthesis reactor comprising an external shell (2), in which at least one catalytic bed (15, 16, 17) is supported which is in fluid communication with cooling means (11) disposed within said shell (2) for cooling the reaction products leaving said at least one catalytic bed (15, 16, 17), and with a nozzle (4) capable of withstanding a maximum temperature lower than the temperature of the reaction products leaving said at least one catalytic bed, said nozzle extending below said shell (2), and being provided with an opening (7) for withdrawing the reaction products leaving said cooling means (11);

providing a boiler (21) for generating high pressure steam outside said shell (2);

connecting the boiler (21) to the shell (2) in proximity of said nozzle (4); and connecting said at least one catalytic bed (15, 16, 17) with an inlet collector (24) in said boiler (21) by means of a conduit (29) extending through said nozzle (4), said conduit having an outer diameter which is smaller than an inner diameter of said nozzle thereby forming an airspace (30) therebetween, said conduit (29) defining a flowpath for the reacted gases from said reactor to said boiler (21), and said airspace (30) defining a flowpath from said boiler (21) to said opening (7).

2. Method according to claim 1, wherein said boiler (21) is connected to the shell (2) by joining a gas outlet nozzle (28) of the boiler (21) to said nozzle (4).

3. Method according to claim 1, wherein said conduit (29) is co-axially extended in said nozzle (4).

4. Method according to claim 1, wherein said at least one catalytic bed (15, 16, 17) is connected to said conduit (29) by means of gas conveying means already existing in said reactor.

5. Method according to claim 4, wherein said conveying means comprise a conduit collector (14) of reaction products leaving from said at least one catalytic bed (15, 16, 17).

6. Method according to claim 1, wherein said boiler (21) is of the shell-and-tube type.

* * * * *